United States Patent [19]
Challis

[11] Patent Number: 4,940,063
[45] Date of Patent: Jul. 10, 1990

[54] ANGULAR DISPLACEMENT MEASURING APPARATUS

[76] Inventor: Brian Challis, No. 9 Northridge Way, Sandy, Utah 84092

[21] Appl. No.: 314,441

[22] Filed: Feb. 23, 1989

[51] Int. Cl.⁵ .............................................. A61B 5/10
[52] U.S. Cl. ..................................... 128/774; 33/512; 33/534
[58] Field of Search ................. 128/774, 782; 33/1 C, 33/1 N, 1 PT, 177, 564, DIG. 13, 511, 512, 534; 73/849

[56] References Cited

U.S. PATENT DOCUMENTS 3,608,541 9/1971 Hall ...................................... 128/781
3,991,745 11/1976 Yoslow et al. ....................... 128/781
4,643,194 2/1987 Fogarty ............................... 128/774

FOREIGN PATENT DOCUMENTS 0217680 1/1985 German Democratic Rep. .................................... 128/774
83/02052 6/1983 PCT Int'l Appl. ................. 128/781
0733650 5/1980 U.S.S.R. .............................. 128/774
1093350 5/1984 U.S.S.R. .............................. 128/782

Primary Examiner—Randall L. Green
Assistant Examiner—K. M. Reichle
Attorney, Agent, or Firm—Thorpe, North & Western

[57] ABSTRACT

Angular displacement measuring apparatus includes a tightly-wound coil spring conduit which, when bent, elongates on the outside of the bend without substantially shortening on the inside of the bend. A wire is disposed within the conduit to extend from one end, where the wire is fixed so that it cannot slide longitudinally relative to the conduit, to the other end, where the wire is free to slide longitudinally relative to the conduit. A movement measuring device is mounted on the other end of the conduit and coupled to the wire for measuring movement of the wire. As the conduit is bent, the wire is caused to move an amount proportional to the degree of the bend and so measurement of the movement of the wire serves as a measure of the degree of the bend, i.e., angle of displacement of the conduit. Bending in an object is determined by attaching the conduit to the object to be measured.

14 Claims, 1 Drawing Sheet

ANGULAR DISPLACEMENT MEASURING APPARATUS

BACKGROUND OF THE INVENTION

This invention relates to apparatus for measuring angular displacement or bending occurring in the apparatus itself or in another object.

The need or desirability of determining the angle of bend of an object is present in a variety of fields including physical therapy, athletic performance measurement, robotics and building structures. In physical therapy where an injured limb or body part is in need of therapy or rehabilitation, it is oftentimes desirable to measure the improvement in the bending range of motion of the limb or part being rehabilitated. At present, this is typically done by strapping the limb or body part into some type of nonportable equipment and then manipulating the equipment to make the measurement. Of course, this requires that the patient travel to the therapist's office or wherever the equipment is located to have the range of motion measurements taken.

In the field of athletic performance measurement, it would be advantageous, at least in some athletic activities, to measure the angular displacement or bending of an athlete's leg, arm, back, etc., while carrying out an activity. The purpose of this might be to determine what angular displacements of the body parts produce the best performance. Presently, such determinations would be made, at least to the extent possible, with video recording of the activity and then later examination of the recording. This approach, however, does not lend itself to precise measurement of angular displacements.

In a variety of other fields, there is a need for simple, inexpensive, convenient and yet accurate bending or angular displacement measurement.

SUMMARY OF THE INVENTION

It is an object of the invention to provide a simple, portable, easy to use and accurate angular displacement measurement device.

It is also an object of the invention to provide such a device which may be readily mounted on the object whose angular displacement is to be measured, and then removed after use.

It is a further object of the invention to provide such a device capable of measuring the angular displacement of an object which may be bent at multiple locations along a locus of points.

It is another object of the invention to provide such a device capable of measuring the angular displacement of an object where a center of bending is either nonexistent or inaccessible.

It is an additional object of the invention to provide such a device capable of measuring the angular displacement of an object which may be bent in any of a variety of directions.

These and other objects of the invention are realized in a specific illustrative embodiment of angular displacement measuring apparatus having a conduit which, when bent, elongates on the outside of the bend without shortening on the inside of the bend, and a fiber disposed in the conduit to extend from one end thereof, where the fiber is fixed so that it may not slide longitudinally relative to the conduit, to and out the other end thereof where it is free to slide relative to the conduit. A movement measuring device is disposed at the other end of the conduit and coupled to the fiber for measuring movement of the fiber relative to conduit as the conduit is bent. Measurement of this movement is then used to calculate the degree of bending of the conduit.

In use, the apparatus would be attached to the object whose bending is to be measured so that the conduit lies generally perpendicular to the direction of bending. Then, as the object is bent, readings of the angular displacement may be made.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Figure 1:
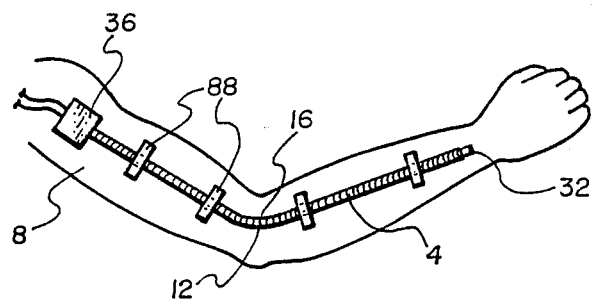
FIG. 1 shows apparatus of the present invention attached to a human arm.
Figure 2:
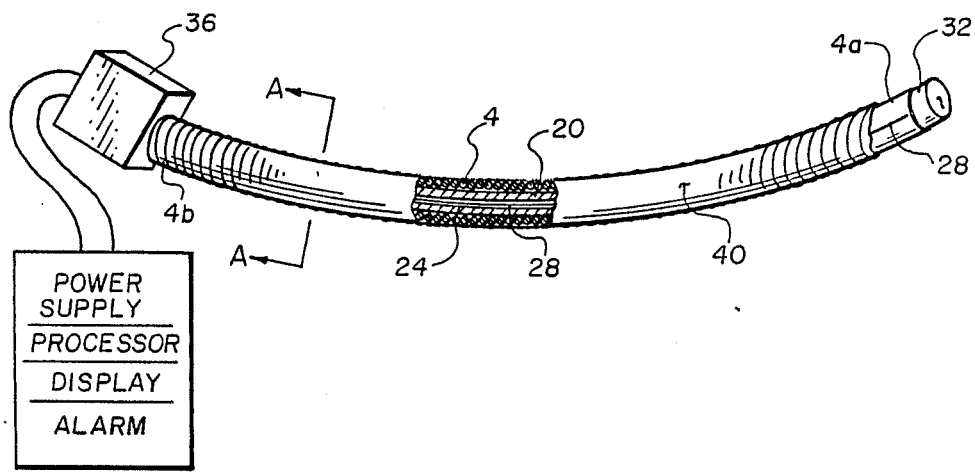
FIG. 2 shows a perspective view of one embodiment of apparatus made in accordance with the principles of the present invention.
Figure 3:
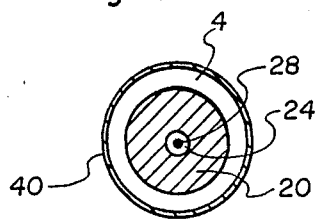
FIG. 3 shows a cross-sectional view of the conduit of the apparatus of FIG. 2, taken along lines A-A.

Referring to FIGS. 1 and 2, there is shown one illustrative embodiment of angular displacement measuring apparatus attached to a person's arm (FIG. 1) and partially cut away to show a portion of the interior thereof (FIG. 2). The apparatus includes a tightly-wound coil spring conduit 4 which, when bent, results in the coil segments on the outside of the bend to separate so that that part of the conduit elongates. Since the coil spring is tightly wound, i.e., adjacent coils touch when in an unflexed condition, there is no compression or shortening of the conduit 4 on the inside of the bend. In FIG. 1 where apparatus of the present invention is shown attached to a person's arm 8, the outside portion 12 of a bend in the conduit 4 would elongate, while the inside portion 16 of the bend would remain substantially unchanged in length. Advantageously, the coil spring conduit 4 is made of stainless steel, other metal alloys, or resin-based composites. Of course, any material which would provide a conduit with the described properties would suffice.

The apparatus also includes an inner sleeve 20 disposed within the conduit 4 to extend substantially along the length thereof. The sleeve 20 has a central bore 24 in which is disposed a fiber 28. The fiber 28 extends from one end 4a of the conduit 4 and sleeve 20, where the fiber is affixed in a plug 32 so that it cannot move longitudinally relative to the conduit, to the other end 4b of the conduit and sleeve, where the fiber is coupled to a movement measuring device 36. The end of the fiber 28 coupled to the measuring device 36 is free to move longitudinally relative to the conduit 4 (and measuring device 36, as will be explained momentarily).

The sleeve 20 serves to reduce friction and wear between the conduit 4 and fiber 28, and to put some space between the conduit and fiber so that any bending of the conduit will cause a greater longitudinal movement of the fiber. In other words, the spacing between the conduit 4 and fiber 28 produced by the sleeve 20 effectively magnifies the amount of longitudinal movement of the fiber for each unit of bending of the conduit.

It is also apparent from the drawings that bending of the conduit 4 at any point along its length will cause a corresponding longitudinal movement of the fiber 28 at the end 4b of the conduit. Thus, there is no single pivot point of the angular displacement measuring apparatus which must be matched to a corresponding pivot point of a limb (e.g., elbow of arm 8 of FIG. 1) whose bending is being measured.

The sleeve 20 might advantageously be made of polytetrafluoroethylene, fused silica, or other flexible, abrasion resistant material. The fiber 28 might be made of stainless steel. In order to protect the coil spring conduit 4 from moisture, dirt, and other contaminants, a thin elastic sheath 40 may be wrapped and preferably heat shrunk about the conduit 4. The sheath 40 might illustratively be made of polytetrafluoroethylene. The sheath 40 may be attached to the conduit 4 in a manner that applies longitudinal compressive force to the conduit, thereby maintaining intimate contact between the coils of the conduit while in a relaxed state.

Figure 4:
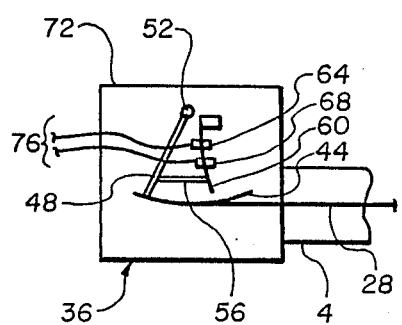
FIG. 4 graphically shows one type of movement measuring device which may be used in the apparatus of the present invention.

The movement measuring device 36 could be any of a variety of devices for measuring movement, in this case, of the fiber 28. For example, strain gages, including magnetic strain gages, capacitance strain gages, acoustic strain gages, etc., could be utilized as the movement measuring device 36. FIG. 4 shows a conventional movement measuring device 36 having a curved fiber guide 44, to which the fiber 28 is attached, a pivot arm 48 mounted to pivot about a pivot axis 52 and attached to the guide 44 for carrying the guide, and a finger 56 also carried by the arm 48 for pressing against and deflecting a load cell or element 60 on which are mounted strain gage pairs 64 and 68. All these elements are carried in a housing 72. As the conduit 4 is bent, the fiber 28 is pulled away from the housing 72 and farther into the conduit to pull the guide 44 and thus the arm 48 toward the conduit. This, in turn, causes the finger 56 to press against and deflect the load cell 60 which deflection is measured by strain gages 64 and 68. Wires 76 carry signals from the strain gages 64 and 68 to a processing and display unit 80 (FIG. 2) which processes the signals to produce a reading of the amount (degree) of angular displacement of the conduit 4. (The degree of angular displacement of the conduit 4 is directly proportional to the longitudinal movement of the fiber 28 at the end 4b of the conduit and so can readily be determined). The processing and display unit 80 could include a conventional microprocessor and display scale along with a power supply.

- An alarm is provided in unit 80 to give an audible and/or visual signal when a certain angular displacement of the conduit 4 is reached. This might be desireable, for example, to alert a person on whom the apparatus is attached that bending of a limb or body part has reached or exceeded a certain critical angle. Any number of positions may be set to activate the alarm 80.

The apparatus is used simply by attaching to the object whose bending is to be measured. The conduit 4 is shown in FIG. 1 attached by tape 88 to the arm 8. Straps or other means could also be used to attach the measuring apparatus, and such attachment could be made to other limbs or body parts such as legs, hips, backs, necks, etc., to measure angular displacement.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. An angular displacement measuring device comprising
    a bendable conduit having a side wall which is stretchable in the direction parallel to the longitudinal axis of the conduit but is substantially noncompressible in the same direction so that when the conduit is bent, the portion of the side wall on the outside of the bend elongates while the portion of the side wall on the inside of the bend remains substantially unshortened,
    a fiber having first and second ends disposed in the conduit so that the first end extends from one end thereof, where the fiber is fixed at the second end of said conduit so that it may not slide longitudinally relative to and out of the other end of the conduit and where the remainder of the fiber is free to slide relative to the remainder of the conduit, and
    movement measuring means disposed at said other end of the conduit and coupled to said fiber for measuring movement of the fiber relative to the conduit as the conduit is bent to thereby measure the angle of bending of the conduit.

2. A device as in claim 1 wherein said conduit comprises a tightly wound coil spring.

3. A device as in claim 2 wherein said coil spring is comprised of stainless steel.

4. A device as in claim 2 wherein said coil spring is comprised of a composite material.

5. A device as in claim 2 further including an elongate sheath disposed snugly about the coil spring.

6. A device as in claim 5 wherein said sheath is comprised of a heat shrinkable, elastic material.

7. A device as in claim 5 wherein said sheath is comprised of polytetrafluoroethylene.

8. A device as in claim 1 further including an inner sleeve disposed in the conduit, said sleeve having an elongate central bore in which the fiber is positioned.

9. A device as in claim 8 wherein said inner sleeve comprises a flexible, synthetic material.

10. A device as in claim 9 wherein said synthetic material is polytetrafluoroethylene.

11. A device as in claim 9 wherein said synthetic material is fused silica.

12. A device as in claim 1 wherein said fiber is comprised of stainless steel.

13. A device as in claim 1 wherein said movement measuring means further comprises display means for producing a visual indication of the angle of displacement of the conduit.

14. A device as in claim 13 wherein said movement measuring means further comprises an alarm means for producing an audible signal when the conduit is bent to a predetermined angle.

* * * * *